United States Patent [19]

Torgersen et al.

[11] Patent Number: 5,340,713
[45] Date of Patent: Aug. 23, 1994

[54] PROCESS FOR THE CHARACTERIZATION OF HUMAN RHINOVIRUSES

[75] Inventors: Helge Torgersen, Purkersdorf; Timothy Skern; Dieter Blaas, both of Wien, all of Austria

[73] Assignee: Boehringer Igelheim International GmbH, Fed. Rep. of Germany

[21] Appl. No.: 541,907

[22] Filed: Jun. 22, 1990

[30] Foreign Application Priority Data

Jun. 24, 1989 [DE] Fed. Rep. of Germany ....... 3920754

[51] Int. Cl.$^5$ .......................... C12G 1/70; C12G 1/68; C12P 19/34; C07H 17/00
[52] U.S. Cl. .......................................... 435/5; 435/6; 435/91.1; 435/91.32; 435/91.33; 435/91.5; 435/91.51; 536/23.72; 536/24.33; 935/16; 935/76; 935/77; C12G/1/70; C12G/1/68; C12P/19/34; C07H/17/00
[58] Field of Search ............... 435/5, 6, 91, 7.1, 91.32, 435/91.33, 91.5, 91.51; 536/23.72, 24.33; 935/16, 76, 77

[56] References Cited

U.S. PATENT DOCUMENTS 4,683,195 7/1987 Mullis et al. .......................... 435/6
5,176,995 1/1993 Sninsky et al. ........................ 435/6

FOREIGN PATENT DOCUMENTS 0229701 7/1987 European Pat. Off. .
0309969 4/1989 European Pat. Off. .
87/02065 4/1987 PCT Int'l Appl. .

OTHER PUBLICATIONS

Gama et al. Amplification of Rhinovirus Specific Nucleic Acids From Clinical Samples Using the Polymerase Chain Reaction, *Journal of Medical Virology*, 28:73-77, Jun. 1989.
Sequence Comparison; RN 140335-31-5.
Sequence Comparison; RN 147 303-32-0.
Morinet et al., Comparison of 17 Isolates of the Human Parvovirus B19 by Restriction Enzyme Analysis, *Arch. Virol.* 90:165-172 (1986).
European Search Report For Corresponding European Application EP 90 11 1950.
Bruce et al., *The Lencet*, p. 53 (Jul. 2, 1988).
Callahan et al., *Proc. Natl. Acad. Sci. USA* 82:732-736 (1985).
Cann et al., *Nucleic Acids Research* 12(20):7787-7792 (1984).
Cooney et al., *Infection and Immunity* 37(2):642-647 (1982).
Gama et al., *Nucleic Acids Research* 16(19):9346 (1988).
Hamparian et al., *Virology* 159:191-192 (1987).
Saiki et al., *Science* 239:487-491 (1988).
Skern et al., *Virology* 136:125-132 (1984).
Skern et al., *Nucleic Acids Research* 13(6):2111-2126 (1985).
Stanway et al., *Nucleic Acids Research* 12(20):7859-7875 (1984).
Stott et al., *Ann. Rev. Microbiol.* 26:503-525 (1971).
Hughes et al., *J. Gen. Virol.* 69:49-58 (1988).

Primary Examiner—Margaret Parr
Assistant Examiner—Bradley L. Sisson
Attorney, Agent, or Firm—Sterne, Kessler, Goldstein & Fox

[57] ABSTRACT

The present invention relates to a method of characterizing viruses and the use thereof for classification. According to the invention, a cDNA copy of a first virus is made and the cDNA is amplified and cleaved using at least one restriction endonuclease. The location of restriction fragments is mapped and compared to that of other viruses. Primers useful for amplifying the cDNA may be derived from sequences found in the 5' non-coding regions of picornavirus including human rhinovirus.

2 Claims, 3 Drawing Sheets

```
                Hind III            270                 290
TACGCAAAGCTTAGTAGCATCTTTGAAATCGTTTGGCTGGTCGATCCGCCATTTCCCCTG
             a   c              t       t    t          t 310                 330                 350
GTAGACCTGGCAGATGAGGCTAGAAATACCCCACTGGCGACAGTGTTCTAGCCTGCGTGG
                              c 390                 410    Ban II
CTGCCTGCACACCCTATGGGTGTGAAGCCAAACAATGGACAAGGTGTGAAGAGCCCCGTG
             g                          t                    Ban II
          Dra III 430                 450                 470
TGCTCGCTTTGAGTCCTCCGGCCCCTGAATGTGGCTAACCTTAACCCTGCAGCTAGAGCA
                                    c                      c a c 490
CGTAACCCAA
a c b) HRV 1 B / HRV 1 A
         210                 230                 250
CTCTAACAGGGCAAAAACAACTGATATCGTTACCCGCAAAGTGCCTACACAGAGCTTAGT
     c                  a   c      t 270   Bgl II         290                 310
AGGATTCTGAAAGATCTTTGGTTGGTCGCTCAGCTGCATACCCAGCAGTAGACCTTGCAG
              Bgl II                             t 330                 350                 370
ATGAGGCTGGACATTCCCCACTGGTAACAGTGGTCCAGCCTGCGTGGCTGCCTGCACA-C
                                                         g  c
                                                         Hin PI
         390                 410
TCTTATGAGGTGTGAAGCCAAAGATTGGACA
     c                  c  t
```

FIG. 2

PROCESS FOR THE CHARACTERIZATION OF HUMAN RHINOVIRUSES

FIELD OF THE INVENTION

The present invention relates to a method of characterising viruses and the use thereof for typing or classification.

BACKGROUND OF THE INVENTION

More than 100 serotypes of human rhinoviruses (HRV), which are the major causes of colds, have been described (Stott & Killington, 1972; Cooney et al., 1982; Hamparian et al., 1987). Although the diseases caused by rhinoviral infections are normally not serious in themselves, they may produce secondary infections in a weakened organism; these secondary infections are of economic and social significance. In spite of the considerable progress made in understanding this group of viruses, effective vaccination has hitherto always been ruled out because of the number of serotypes. Diagnosis of a rhinovirus and determination of the serotype circulating within a population can at present only be achieved by complex serological analysis (Cooney et al., 1982; Kellner et al., 1988).

One object of the present invention was to develop a simplified method of classification of viruses, particularly rhinoviruses.

Hitherto, the nucleotide sequences of the RNA genomes from 4 HRV strains have been determined: HRV1B (Hughes et al., 1988), HRV2 (Skern et al., 1985), HRV14 (Stanway et al., 1984; Callahan et al., 1985) and HRV89 (Duechler et al., 1987). Analysis of the sequences showed that there are significant areas of identical sequences within the 5'-non-coding regions of these and other picornaviral genomes (Rivera et al., 1988). Two such blocks (the bracketed sequences) are conserved in the four rhinovirus serotypes which have been sequenced hitherto.

These blocks have, on the one hand, 23 identical nucleotides, namely between nucleotides #531 and 553 (1st bracketed sequence) and a further 21 identical nucleotides between numbers #161 and 181 (2nd bracketed sequence). Unless otherwise stated, the positional data refer to the numbering of HRV2 (Skern et al., 1985, FIG. 2, pages 2117–2121).

SUMMARY OF THE INVENTION

The present invention therefore relates to a method of characterising viruses, characterised in that
a) the RNA of the virus is converted into cDNA,
b) the cDNA is amplified in the presence of primers 1 and 2 of the areas of identical sequences using the polymerase chain reaction,
c) the amplified DNA is analysed using various restriction enzymes and
d) the restriction pattern obtained is compared with the restriction pattern of known viruses.

The primer 1 may preferably be derived from the first bracketed sequence of identical nucleotides and the primer 2 may preferably be derived from the 2nd bracketed sequence of the rhinoviruses. Preferably, primer 2 is used in step A of the process according to the invention.

The process according to the invention is particularly suitable for characterising rhinoviruses, preferably human rhinoviruses. The oligonucleotides of sequence #161 to 178 of HRV2 may preferably be used as primer 1 and the oligonucleotides complementary to sequence #531 to 544 of HRV2 are preferably used as primer 2.

BanII, HindIII, RsaI, EcoRI, BglII, PvuII, DraIII and HinPI have proved particularly suitable restriction enzymes for characterising rhinoviruses.

The process according to the invention can be used for typing viruses, particularly rhinovirus, preferably human rhinoviruses.

DESCRIPTION OF THE FIGURES

FIG. 2: Relationship between human rhinovirus serotypes in the 5'-non-coding region.
a) HRV2 and HRV49

The HRV2 sequence from nucleotide 241 to 490 is shown. Differences between this and the HRV49 sequence (determined from the nucleotides corresponding to 241 to 482) are given below.
b) HRV1A and HRV1B The HRV1B sequence from nucleotide 203 to 412 is given. Differences between this and the HRV1A sequence (determined from the corresponding region) are given below. A dash indicates the deletion of a nucleotide. The restriction sites used are shown.

FIG. 3: Polyacrylamide gel analysis of the fragments obtained by restriction enzyme digestion of the amplified DNA.
A) BanII positive serotypes
B) BanII negative serotypes The amplified DNA fragments were digested with the enzymes given in Table 1. The serotypes and enzymes are given above the individual bands.

Abbreviations: Ba: BanII, Bg: BglII; Dr: DraIII; Ec: EcoRI; Hi: HinPI; Hd: HindIII; Pv: PvuII; Rs: RsaI; m: marker. The sizes of the markers are indicated in base pairs.

DETAILED DESCRIPTION OF THE INVENTION

According to the invention, oligonucleotides from these regions have been used to amplify sequences of rhinoviral serotypes by means of the recently developed "polymerase chain reaction" (PCR; Saiki et al., 1988, protocols in the legends to FIGS. 1–6, and bibliographic reference citation number). The polymerase chain reaction makes it possible to carry out enzymatic amplification even of unknown DNA sequences in vitro. For this purpose, two oligonucleotide primers which flank the DNA fragment to be amplified have been used. These primers are constructed so that one binds to the (+)-strand and the other to the (−)-strand and are oriented so that the DNA synthesis is effected by the DNA polymerase through the region located between the primers. As a result of the multiple, preferably up to thirty-fold repetition of a cycle of three steps, namely: 1) heat denaturing of the DNA; 2) binding of the primers to the complementary sequences; 3) extension with DNA polymerase (the quantity of DNA fragment being doubled in each cycle), there as exponential increase in the DNA fragment flanked by the primers. The PCR can be made automatic by the preferred use of a thermostable DNA polymerase obtained, for example, from the bacterium *Thermus aquaticus*.

Figure 1:
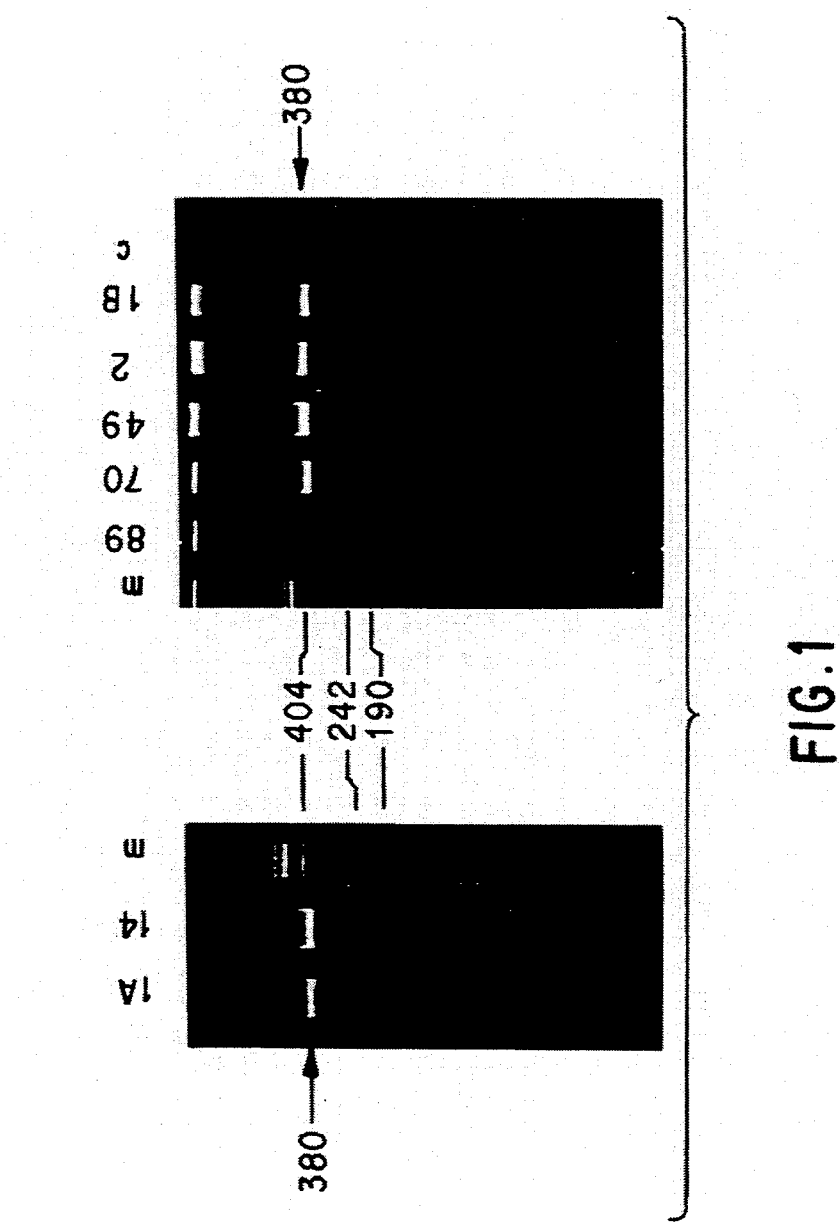
FIG. 1: Polyacrylamide gel analysis of the PCR products. Aliquots of amplified cDNA obtained from an RNA which had been isolated from crude lysate preparation (serotypes 1B, 2, 49, 70 and 89) or from HeLa lysates infected with rhinovirus (serotypes 1A and 14). The serotypes are given at the top of the bands; m: marker DNA; c: control with RNA isolated from non-infected HeLa cells. The sizes (in base pairs) are given both for three marker fragments and also for the amplified fragment.

As has been shown, the conservation of these regions extends not only to the rhinovirus serotypes the structure of which has already been explained but also at least to three serotypes which were hitherto structurally unknown. Surprisingly, it was possible to generate a DNA fragment of the rhinoviruses HRV1A, HRV49 and HRV70 using PCR and specific primers 1 and 2 (FIG. 1).

Two primers derived from the conserved regions therefore offer the possibility of using them universally in order to amplify even unknown DNA sequences. These primers, particularly an 18-mer and a 14-mer, preferably the oligonucleotide primer 1 (sequence #161 to 178) and the oligonucleotide primer 2 (complementary to the sequence #531 to 544), which had been prepared using known methods of oligonucleotide synthesis, therefore form the basis of the method of typing according to the invention.

In order to type viruses or serotypes of viruses it is necessary to indicate characteristic differences between the individual examples. Hitherto, as already mentioned, typing has been performed using the reaction with antibodies and the cross-reactivities have been determined. Another possibility is the discovery of structural differences; a method which is hardly normally a rapid and simple diagnostic method, structural analysis is generally extremely laborious. On the other hand, typing on the basis of structural distinguishing features can be regarded as giving a high degree of certainty.

The aim of the present invention was therefore to develop a method of typing which makes use of structural differences between different viruses. This has been achieved by using "indicators" determined according to the invention to discover structural differences.

In the case of DNA or RNA these "indicators" may be special restriction enzyme recognition sites. (The method is generally applicable to nucleic acid sequences insofar as RNA can be transcribed into DNA by reverse transcription.) As is known to those skilled in the art, restriction enzymes in general are extremely specific. Thus, in a number of cases, even the changing of a base within a special recognition sequence may result in the special restriction enzyme no longer recognising the sequence.

In order to discover these specific "indicators" for the rhinoviruses, for example, the amplified fragments both of the structurally known rhinovirus serotypes and also of the rhinovirus serotypes which have hitherto been structurally unknown were compared with one another.

Surprisingly, the four structurally known serotypes show significant differences between the region of identical bracketed sequences, in spite of the high level of conservation. The resulting characteristic differences in the restriction pattern of each serotype, which are also present in the amplified fragments starting from these regions, are used according to the invention to solve the problem on which the invention is based.

Since there was no sequence information available on HRV1A, HRV49 and HRV70, the DNA sequence from the amplified fragments of HRV1A and HRV49 was determined in order to discover whether there are any characteristic restriction sites present. This result correlates well with the level of cross-reactivity between these pairs (Cooney et al., 1982). The differences between the sequences of HRV2 and HRV49 and between those of HRV1A and HRV1B are illustrated in FIGS. 2a and 2b, respectively. In all, 15 base exchanges and 2 deletions were observed between HRV2 and HRV49 within the 241 sequenced base pairs. Among the 210 bp of HRV1A and HRV1B which were analysed, 9 base exchanges and 1 insertion was observed. These changes resulted in both cases in the formation or loss of one or more restriction cutting sites (see FIG. 2). Therefore, by using this amplification experiment, it was possible to demonstrate that characteristic cutting sites can be selected for each serotype.

Figure 3A:
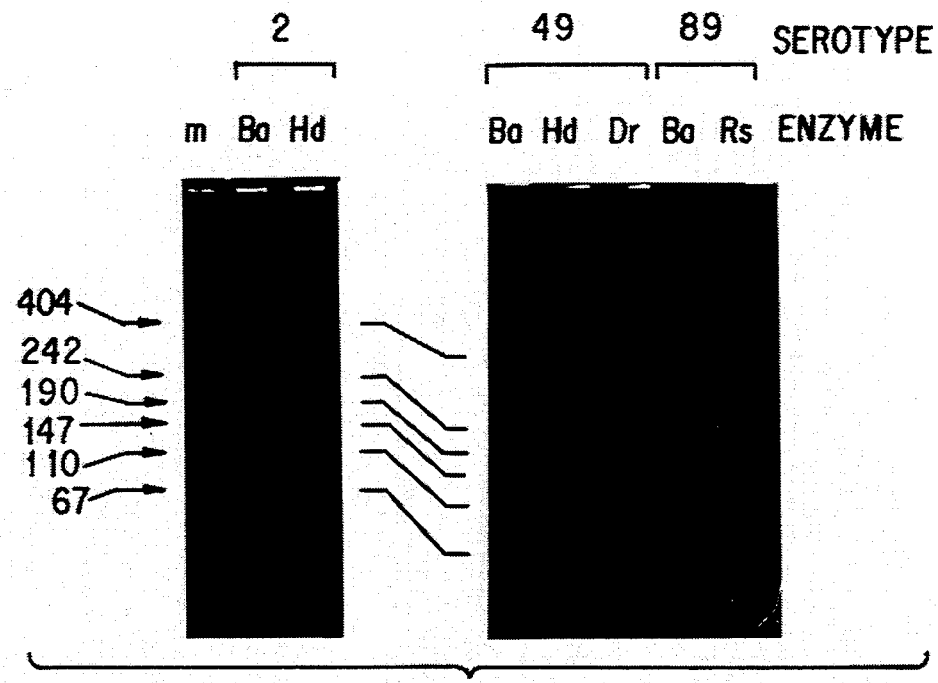
Figure 3B:
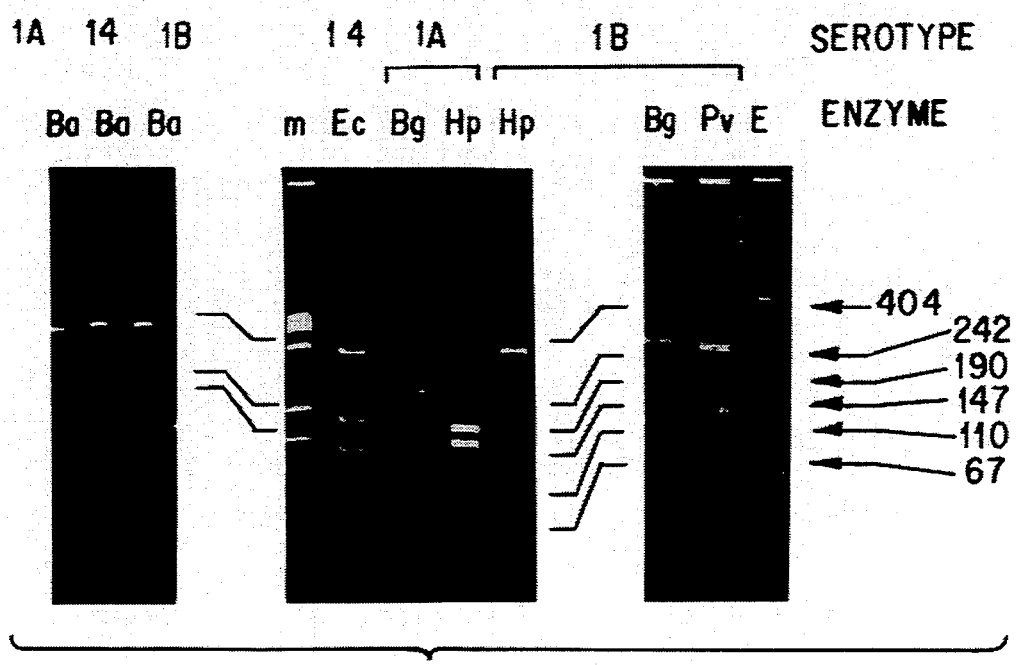

In order to solve the problem of the invention, restriction enzymes with which the serotypes could be identified without any doubt were selected; Table 1 shows the selected enzymes together with the fragment sites for the rhinoviral system. A comparison of the DNA fragments showed that the fragments of HRV2, HRV49 and HRV89 have a cutting site for the BanII (FIG. 3a), but that the fragments of HRV1A, HRV1B and HRV14 did not (FIG. 3b). Preferably, by using this enzyme, the serotypes can therefore be divided into two groups and identification of the serotypes will thus be made easier: the amplified fragments of each serotype were cut with BanII and the products were analysed on polyacrylamide gels. The different fragment length obtained with HRV2 and HRV89 also make it possible to identify these serotypes, as shown in FIG. 3a. The characteristic HindIII site of HRV2 and the RsaI site of HRV89 confirmed this identification. HRV2 could be distinguished from HRV49 by the absence of the HindIII site in the latter.

The serotypes which had no BanII site (FIG. 3b) were identified as follows: HRV14 was identified by means of the EcoRI site. HRV1B and HRV1A both have a BglII site at the same position; here, the presence of an HinPI site in the HRV1A made it possible to distinguish clearly between the two serotypes.

According to the invention it is, therefore, surprisingly possible to type even unknown viruses. Thus, for example, if the 6 serotypes were present in a blind experiment, HRV2, HRV49 and HRV89 could be clearly identified by digestion with BanII and then with HindIII.

A check on the data banks showed that the primers according to the invention are also suitable for amplifying RNA of all strains of polio virus type 1 and 2, but only of strain 23127 of type 3 (Cameron 1988). It is also known that polio virus is secreted from the nasal membranes of patients who have been given the sabin vaccine; RNA of types 1 and 2 would therefore also be amplified in a typing test according to the invention. If, however, the considerable degree of difference between rhinovirus and polio virus is taken into account, there are characteristic restriction sites for polio virus which will rule out any misinterpretation. On the other hand, the primers can also be used advantageously to check the rapidity of the U/C change at position 472 of polio virus, a change which has been shown to be responsible for the virulence and occurs during the passage of the sabin strains in humans (Cann et al., 1984). Under stringent conditions of amplification, no amplification of Coxsackie viruses can be expected with these primers.

The availability of this rapid method according to the invention for typing viruses will make it possible to identify, for example, the rhinovirus serotypes circulating within a population and thereby facilitate epidemiological studies. In order to determine the presence of any particular virus, washings of nasal secretions are routinely introduced into HeLa cells; this is necessary in order to obtain sufficient quantities for further analysis. The quantity of material required for an amplification experiment, in the experiments described here, is similar to that which is obtained after a single passage; however, it is advisable to work directly with the washings of nasal secretion, as described by Gama et al., (1988, page 74, column 1, in the Materials and Methods sections denoted "Samples" and "Extraction of Nucleic Acids", and page 74, column 2, eight lines from the bottom, to page 75, column 1, lines 1–19, page 75, column 2, lines 2–23, and FIG. 1). It was even possible to amplify the cDNA from an RNA isolated from a single plaque using the primers used here. It was recently reported that oligonucleotides which were complementary to sequences from the 5'-non-coding regions of rhinoviruses can be used to detect rhinovirus RNA of more than 50 serotypes in nasal secretions (Bruce et al., 1988). It is possible that the primers described here may be used in conjunction with a similar hybridisation assay in order to improve the sensitivity and make it possible to distinguish between different serotypes.

To sum up: it has been shown that PCR can be used in conjunction with two universal primers to amplify a DNA fragment from various rhinovirus serotypes. By using various specific restriction enzymes on these amplified fragments it was then possible to distinguish between the different serotypes. The present invention relates to a method which can be used to type viruses which have an arrangement of conserved sequence blocks between different serotypes, particularly rhinoviruses.

Initially it will still be necessary to sequence the amplified DNA of viruses which have no known restriction enzyme pattern and to identify the serotype by means of antibodies. In this way it will be possible to establish a catalogue of restriction enzyme patterns of, for example, all rhinovirus serotypes and this catalogue could then be regularly and continuously updated and in the long-term will make it unnecessary to carry out typing using antibodies. Viruses characterised in this way might be, for example: HIV, Foot and Mouth Disease virus, Echoviruses and Coxsackie viruses.

Using this catalogue and the method according to the invention it is therefore possible to carry out rapid characterisation and typing of viruses.

EXAMPLE 1

Production of Crude Lysate Preparations of the HRV Strains

All the virus serotypes were obtained from the ATCC and plaque-purified. HeLa cells (Ohio strain) were cultivated in 150 cc T flasks and infected with the HRV strains at an MOI of about 1 as described in Skern et al., (1984, page 126, column 2, first paragraph). The quantity of virus was usually $10^9$ PFU in 30 ml of medium. After two cycles of freezing and thawing in order to lyse the cells the medium was freed from cell debris by centrifuging at low speed. The virus was concentrated out of the medium using polyethyleneglycol 6000 (PEG) and resuspended in 1 ml of phosphate-buffered saline solution. When infected HeLa lysates were used the PEG precipitation was omitted.

EXAMPLE 2

Reverse Transcription of the Viral RNA

The RNA was prepared by treating 0.1 to 0.5 ml of the viral, PEG concentrated suspension or 0.5 ml of non-concentrated suspension with 1% SDS and 10 mM EDTA. After extraction with phenol/chloroform 2 $\mu$g of the carrier tRNA were added and the RNA was precipitated with ethanol. The cDNA was prepared by placing the entire RNA preparation, 10 pmol of primer 2 and 10 units of reverse transcriptase (Super RT, Anglian Biotechnology) in 20 $\mu$l final volume in accordance with the manufacturer's instructions. Initially, the cDNA was purified by extraction with phenol/chloroform and ethanol precipitation; in later experiments, the cDNA mixture was used directly for the polymerase chain reaction.

EXAMPLE 3

Polymerase Chain Reaction

The polymerase chain reaction (PCR) was carried out in a total volume of 50 $\mu$l with 10 $\mu$l of the cDNA preparation, 100 pmol each of primer 1 and primer 2, 0.4 mM of all four dNTPs, 2 units of *Thermus aquaticus* DNA polymerase (Cetus) in the buffer made by Cetus Corp., using the apparatus described by Torgesen et al., (1989), for 30 cycles at a setting of 92° C. (2 minutes), 40° C. (3 minutes) and 70° C. (3 minutes). 10 $\mu$l of the reaction mixture were analysed directly on a 6% polyacrylamide gel (Maniatis et al., 1982). Restriction analysis was carried out on aliquots of the amplified DNA, using the enzymes shown in Table 1; the products were analysed on 6% polyacrylamide gel.

The dideoxy sequencing method according to Sanger was used for sequencing (Sanger et al., 1977). The double-stranded DNA obtained after the PCR was electroeluted from the polyacrylamide gel and sequenced using primers 1 and 2 and the modified T7 polymerase (Pharmacia) in accordance with the manufacturer's instructions. Computer analysis of the DNA sequences was carried out using the Staden programmes modified by Isono (Isono, 1982).

Results

Comparison of the nucleotide sequences of HRV1B (Hughes et al., 1988), HRV2 (Skern et al., 1985) and HRV89 (Duechler et al., 1987) showed that the regions between nucleotides #161 and 181 and nucleotides #531 and 553 were identical (the numbering was in accordance with HRV2, Skern et al., 1985). Surprisingly, the four serotypes show significant differences from one another between these regions of identical bracketed sequences. The resulting characteristic differences in the restriction pattern of each serotype, which are also present in the amplified fragments starting from these regions, are used according to the invention to solve the problem on which the invention is based. Two primers were synthesised for this purpose, oligonucleotide primer 1 (sequence #161 to 178; CAAGCACTTCTGTTTCCC) and oligonucleotide primer 2 (complementary to #531 to 544: ACTACTTTGGGTGT). The cDNA was prepared from viral RNA and amplified using primers 1 and 2 as described above.

FIG. 1 shows the polyacrylamide gel analysis of an amplification experiment in which 7 different HRV serotypes were used. In each case, a DNA fragment of approximately 380 bp was generated (corresponding to the distance between the two primers). It was demonstrated that the primers are capable of binding to the cDNA of not only HRV1A but also HRV49 and HRV70, implying that the corresponding sequences are also present in these serotypes. Since there was no available sequence information on HRV1A, HRV49 and HRV70, the DNA sequence from the amplified fragments of HRV1A and HRV49 was determined in order to find out whether characteristic restriction sites are present. 241 bp of the sequence for HRV49 and 210 bp for HRV1A were obtained. Computer analysis showed that the sequence of HRV49 is closely related to that of HRV2 and the sequence of HRV1A is closely related to that of HRV1B (in order to increase the accuracy of the HRV49 sequence, the sequencing reactions were carried out in parallel using primers 1 and 2 on a plasmid which contained the HRV2 5'-non-coding region, so that the differences were clearly detectable). The differences between the sequences of HRV2 and HRV49 and between those of HRV1A and HRV1B are shown in FIGS. 2a and 2b. In all, 15 base exchanges and 2 deletions between HRV2 and HRV49 were observed within the 241 base pairs sequenced. Among the 210 bp of HRV1A and HRV1B which were analysed, 9 base exchanges and 1 insertion were observed. In both cases these changes resulted in the formation or loss of a restriction cutting site (as shown in FIG. 2, one HindIII site was lost and one DraIII site was created in HRV49, as compared with HRV2). Therefore, using this amplification experiment, it was possible to demonstrate that characteristic cutting sites can be selected for each serotype.

In order to solve the problem according to the invention, restriction enzymes were selected with which the serotypes can be identified without any doubt; Table 1 shows the enzymes selected together with the fragment sites. For HRV1A and HRV49 it was presumed that no further sites for the corresponding enzymes are present in the unknown region. A comparison of the DNA fragments showed that the fragments of HRV2, HRV49 and HRV89 have a cutting site for enzyme BanII (FIG. 3a), but the fragments of HRV1A, HRV1B and HRV14 do not (FIG. 3b). Preferably, the serotypes can be divided into two groups using this enzyme: in order to simplify the identification of the serotypes, the amplified fragments of each serotype cut with BanII and the products were analysed on polyacrylamide gels. The different fragment length obtained with HRV2 and HRV89 also make it possible to identify these serotypes, as shown in FIG. 3a. The characteristic HindIII site of HRV2 and the RsaI site of HRV89 confirmed the identification (the 96 bp RsaI fragment was too faint to be seen on this gel). HRV2 and HRV49 were distinguished by the absence of the HindIII site from HRV49.

The serotypes which have no BanII site (FIG. 3b) were identified as follows: HRV14 was identified by means of the EcoRI site (there was partial digestion). HRV1B and HRV1A both have a BglII site in the same position; here, the presence of an HinPI site in the HRV1A made it possible to distinguish clearly between the two serotypes. As only two fragments were obtained with HinPI, the site marked in FIG. 2 must in fact be the only one in the amplified fragment.

Bibliography

Bruce, C. B., Al-Nakib, W., Tyrell, D. A. J. and Almond, J. W. (1988). Synthetic oligonucleotides as diagnostic probes. Lancet, 8601, 53.

Callahan, P. L., Mizutani, S., and Colonno, R. J. (1985). Molecular cloning and complete sequence determination of RNA sequence of human rhinovirus type 14. Proc. Natl. Acad. Sci. U.S.A., 82 732–736.

Cameron, G. N. (1988). The EMBL data library. Nucleic Acids Res., 16, 1865–1867.

Cann, A., Stanway, G., Huges, P. J., Evans, D. M. A., Schild, C. C. and Almond, J. W. (1984). Reversion to neurovirulence of the live-attenuated Sabin type 3 oral poliovirus vaccine. Nucleic Acids Res., 12, 7787–7792.

Cooney, M. K., Fox, J. P. and Kenney, G. E. (1982). Antigenic groupings of 90 rhinovirus serotypes. Infect. Imm., 37, 642–647.

Duechlef, M., Skern, T., Sommergruber, W., Neubauer, Ch., Gruendler, P., Fogy, I., Blaas, D. and Kuechler, E. (1987). Evolutionary relationships within the human rhinovirus genus; comparison of serotypes 89, 2 and 14. Proc. Natl. Acad. Sci. U.S.A., 84, 2605–2609.

Gama, R. E., Hughes, P. J., Bruce, C. B. and Stanway, G. (1988). Polymerase chain reaction amplification of rhinovirus nucleic acids from clinical material. Nucleic Acids Res., 16, 9346.

Hamparian, V. V., Colonno, R. J., Cooney, M. K., Dick, E. C., Gwaltney, J. M., Jr. Hughes, J. H., Jordan, W. S., Kapikian, A. Z., Mogabgab, W. J., Monto, A., Philips, C. A., Rückert, R. R., Schieble, J. H., Stott, E. J. and Tyrell, D. A. J. (1987). A collaborative report: Rhinoviruses - Extension of the numbering system from 89 to 100. Virology, 159, 191–192.

Hughes, P. J., North, C., Jellis, C. H., Minor, P. D. and Stanway, G. (1988). The nucleotide sequence of human rhinovirus 1B: molecular relationships within the rhinovirus genus. J. Gen. Virol., 69, 49–58.

Isono, K. (1982). Computer programs to analyse DNA and amino acid sequence data. Nucleic Acids. Res., 10, 85–89.

Kellner, G., Popow-Kraupp, T., Kundi, M., Binder, C., Mallner H. and Kunz, C. ( 1988 ). Contribution of rhinoviruses respiratory infections in childhood: a prospective study in a mainly hospitalized infant population. J. Med. Virol., 25, 455–469.

Maniatis, T., Fritsch, F. and Sambrook, J. (1982). Molecular cloning, a laboratory manual. Cold Spring Harbour Laboratory, Cold Spring Harbour, New York.

Rivera, V. M., Welsh, J. D. and Maizel, J. V. (1988). Comparative sequence analysis of the 5'non-coding region of enteroviruses and rhinoviruses. Virology 165, 42–50.

Saiki, R. K., Gelfand, D. H., Stoffel, S., Scharf, St. J., Higuchi, R., Horn, G. T., Mullis, K. B. and Erliche, H. A. (1988). Primer directed enzymatic amplification of DNA with a thermostable DNA polymerase. Science 239, 487–491.

Sanger, F., Nickley, S. and Coulson, A. R. (1977). DNA sequencing with chain-terminating inhibitors. Proc. Natl. Acad. Sci. U.S.A., 74, 5463–5467.

Skern, T., Sommergruber, W., Blaas, D., Pieler, Ch. and Kuechler, D. (1984). Relationship of human rhinovirus strain 2 and poliovirus as indicated by comparison of the polymerase gene regions. Virology 136, 125–132.

Skern, T., Sommergruber, W., Blaas, D., Gruendler, P., Fraundorfer, F., Pieler, C., Fogy, I. and Kuechler, B. (1985). Human Rhinovirus 2: Complete nucleotide sequence and proteolytic processing signals in the capsid protein region. *Nucleic Acids Res.*, 13, 211-2126.

Stanway, G., Hughes, P. J., Mountford, R. C., Minor, P. D. and Almond, J. W. (1984). The complete nucleotide sequence of a common cold virus: human rhinovirus 14. *Nucl. Acids. Res.*, 12, 7859-7875.

Stott, E. J. and Killington, R. A. (1972). Rhinoviruses. *Ann. Rev. Microbiol.*, 26, 503-525.

Torgersen, H., Blaas, D. and Skern, T. (1989). Low cost apparatus for primer-directed DNA amplification. *Anal. Biochem.*, 176, 33-35.

|  | HRV1A | HRV1B | Serotype HRV2 | HRV14 | HRV49 | HRV89 |
|---|---|---|---|---|---|---|
| Ban II | — | — | 255 / 129 | — | 255 / 129 | 298 / 90 |
| BglII | 281 / 106 | 281 / 106 | — | — | — | — |
| DraIII | — | — | — | — | 212 / 172 | — |
| EcoRI | — | — | — | 215 / 165 | — | — |
| HinPI | 208 / 179 | — | NU | — | NU | — |
| HindIII | — | — | 297 / 87 | — | — | — |
| PvuII | NU | 260 / 127 | — | — | — | — |
| RsaI | NU | — | — | NU | — | 294 / 94 |

—in place thereof.

We claim:

1. A method for serotyping a human rhinovirus, comprising:

(a) making a cDNA copy of the RNA sequence of a human rhinovirus to be typed;

(b) amplifying said cDNA obtained by polymerase chain reaction with a first primer CAAGCACTTCTGTTTCCC and a second primer ACACCCAAAGTAGT;

(c) digesting said cDNA and performing a restriction analysis of said digested cDNA fragments wherein said restriction analysis comprises the use of one or more restriction enzymes selected from the group consisting of BanII, HindIII, RsaI, EcoRI, BglII, PvuII, DraIII, and HinPI in combination with said digested cDNA fragments to generate a restriction map; and (d) comparing said restriction map to at least one other restriction map of a human rhinovirus to determine the serotype of said human rhinovirus.

2. The method of claim 1 wherein said human rhinovirus is selected from the group consisting of HRV1A, HRV1B, HRV2, HRV14, HRV49 and HRV89.

* * * * *